(12) United States Patent
Ward et al.

(10) Patent No.: US 11,499,182 B2
(45) Date of Patent: Nov. 15, 2022

(54) PCR METHOD

(71) Applicant: Salisbury NHS Foundation Trust, Salisbury (GB)

(72) Inventors: Daniel Leonard Ward, Salisbury (GB); Christopher John Mattocks, Salisbury (GB)

(73) Assignee: Salisbury NHS Foundation Trust, Salisbury (GB)

( * ) Notice: Subject to any disclaimer, the term of this patent is extended or adjusted under 35 U.S.C. 154(b) by 0 days.

(21) Appl. No.: 15/558,927

(22) PCT Filed: Mar. 3, 2016

(86) PCT No.: PCT/GB2016/050558
§ 371 (c)(1),
(2) Date: Sep. 15, 2017

(87) PCT Pub. No.: WO2016/146968
PCT Pub. Date: Sep. 22, 2016

(65) Prior Publication Data
US 2018/0073053 A1    Mar. 15, 2018

(30) Foreign Application Priority Data
Mar. 17, 2015 (GB) ..................... 1504464

(51) Int. Cl.
*C12P 19/34* (2006.01)
*C12Q 1/686* (2018.01)
*C12Q 1/6876* (2018.01)

(52) U.S. Cl.
CPC ........... *C12Q 1/686* (2013.01); *C12Q 1/6876* (2013.01)

(58) Field of Classification Search
USPC ......... 435/6.1, 6.11, 6.12, 91.1, 91.2, 91.51; 436/94, 501; 536/23.1, 24.3, 24.33
See application file for complete search history.

(56) References Cited

U.S. PATENT DOCUMENTS

| | | | |
|---|---|---|---|
| 6,207,242 B1* | 3/2001 | Chou et al. .......... | C12Q 1/6848 |
| 2013/0096033 A1* | 4/2013 | Routenberg ............ | C40B 50/06 506/26 |
| 2014/0274774 A1* | 9/2014 | Li ........................ | C12Q 1/6858 506/9 |
| 2014/0370507 A1* | 12/2014 | Wittwer ............... | C12Q 1/6883 435/6.11 |

FOREIGN PATENT DOCUMENTS

| | | |
|---|---|---|
| EP | 2770065 A1 | 8/2014 |
| WO | 200214534 A2 | 2/2002 |
| WO | 2003097794 A2 | 11/2003 |
| WO | 2007062495 A1 | 6/2007 |
| WO | 2007130967 A2 | 11/2007 |
| WO | 2010057525 A1 | 5/2010 |
| WO | 2012054933 A2 | 4/2012 |

OTHER PUBLICATIONS

Mullis, Scientific American 262 (4), 56 (1990).*
International Search Report, PCT/GB2016/050558, dated Jun. 14, 2016, 5 pages.
Patents Act 1977: Search report under section 17, GB1504464.7, dated Dec. 7, 2015, 1 page.

* cited by examiner

*Primary Examiner* — Frank W Lu

(57) ABSTRACT

A method for generating amplicon constructs of a target sequence is disclosed, the method comprising providing a target sequence; an oligonucleotide probe, comprising a universal sequence and further comprising, at or towards its 5' end, a target specific sequence capable of hybridising to the reverse complement of a sequence at, or flanking one of the 3' ends of the target sequence; a universal primer, comprising at its 3' end a sequence capable of hybridising to the universal sequence of the oligonucleotide probe and performing a Polymerase Chain Reaction (PCR).

16 Claims, 10 Drawing Sheets
Specification includes a Sequence Listing.

FIGURE 3

Target Sequence W – (Expected amplicon size: 269 base pairs):

Target Sequence X – (Expected size: 225 base pairs):

Target Sequence T (Expected size: 206 base pairs):

Target Sequence U (Expected size: 209 base pairs):

Target Sequences A to L:

Target Sequences M to X:

Target Sequences C-NB, N-NB, W-NB and X-NB:

SEQUENCE LISTING

```
<160> NUMBER OF SEQ ID NOS: 16

<210> SEQ ID NO 1
<211> LENGTH: 57
<212> TYPE: DNA
<213> ORGANISM: Homo sapiens

<400> SEQUENCE: 1
aggaggtgaa tcaactctgg gctggcctgg gctactattc tcgttggccg gcggctg      57

<210> SEQ ID NO 2
<211> LENGTH: 56
<212> TYPE: DNA
<213> ORGANISM: Homo sapiens

<400> SEQUENCE: 2
tcctccactt agttgagacc cgaccggacc cgatgataag agcaccggcc gccgac       56

<210> SEQ ID NO 3
<211> LENGTH: 37
<212> TYPE: DNA
<213> ORGANISM: Homo sapiens

<400> SEQUENCE: 3
cccagagttg attcacctcc tagatcggaa gagcgtc                            37

<210> SEQ ID NO 4
<211> LENGTH: 34
<212> TYPE: DNA
<213> ORGANISM: Homo sapiens
```

```
<400> SEQUENCE: 4
ctcgtggccg gcggctggcg aatttcgacg atcg                                34

<210> SEQ ID NO 5
<211> LENGTH: 70
<212> TYPE: DNA
<213> ORGANISM: Homo sapiens

<400> SEQUENCE: 5
aatgatacgg cgaccaccga gatctacact gaaccttaca ctctttccct acacgacgct    60
cttccgatct                                                          70

<210> SEQ ID NO 6
<211> LENGTH: 65
<212> TYPE: DNA
<213> ORGANISM: Homo sapiens

<400> SEQUENCE: 6
caagcagaag acggcatacg agatgtcgtg attcgcgagt taatgcaacg atcgtcgaaa    60
ttcgc                                                               65

<210> SEQ ID NO 7
<211> LENGTH: 33
<212> TYPE: DNA
<213> ORGANISM: Homo sapiens

<400> SEQUENCE: 7
acactctttc cctacacgac gctcttccga tct                                 33

<210> SEQ ID NO 8
<211> LENGTH: 37
<212> TYPE: DNA
<213> ORGANISM: Homo sapiens

<400> SEQUENCE: 8
ctgcgagaag gctagatcct ccacttagtt gagaccc                             37

<210> SEQ ID NO 9
<211> LENGTH: 34
<212> TYPE: DNA
<213> ORGANISM: Homo sapiens

<400> SEQUENCE: 9
ctcgtggccg gcggctggcg aatttcgacg atcg                                34

<210> SEQ ID NO 10
<211> LENGTH: 33
<212> TYPE: DNA
<213> ORGANISM: Homo sapiens

<400> SEQUENCE: 10
cgcttaaagc tgctagcaac gtaattgagc gct                                 33

<210> SEQ ID NO 11
<211> LENGTH: 54
<212> TYPE: DNA
<213> ORGANISM: Homo sapiens

<400> SEQUENCE: 11
acactctttc cctacacgac gctcttccga tctaggaggt gaatcaactc tggg          54
```

```
<210> SEQ ID NO 12
<211> LENGTH: 56
<212> TYPE: DNA
<213> ORGANISM: Homo sapiens

<400> SEQUENCE: 12
aggaggtgaa tcaactctgg gctggcctgg gctactattc tcgtggccgg cggctg        56

<210> SEQ ID NO 13
<211> LENGTH: 56
<212> TYPE: DNA
<213> ORGANISM: Homo sapiens

<400> SEQUENCE: 13
tcctccactt agttgagacc cgaccggacc cgatgataag agcaccggcc gccgac        56

<210> SEQ ID NO 14
<211> LENGTH: 50
<212> TYPE: DNA
<213> ORGANISM: Homo sapiens

<400> SEQUENCE: 14
gagcaccggc cgccgaccgc ttaaagctgc tagcaacgta attgagcgct              50

<210> SEQ ID NO 15
<211> LENGTH: 71
<212> TYPE: DNA
<213> ORGANISM: Homo sapiens

<400> SEQUENCE: 15
acactctttc cctacacgac gctcttccga tctaggtggc gaatttcgac gatcgttgca   60
ttaactcgcg a                                                        71

<210> SEQ ID NO 16
<211> LENGTH: 71
<212> TYPE: DNA
<213> ORGANISM: Homo sapiens

<400> SEQUENCE: 16
tgtgagaaag ggatgtgctg cgagaaggct agatccaccg cttaaagctg ctagcaacgt   60
aattgagcgc t                                                        71
```

PCR METHOD

CROSS-REFERENCE TO RELATED APPLICATIONS

This application is a 371 of PCT/GB2016/050558 filed Mar. 3, 2016 which claims priority to GB application No. 1504464.7 filed Mar. 17, 2015.

BACKGROUND OF THE INVENTION

Field of the Invention

The present invention relates to a novel method for generating amplicon constructs of a DNA or complimentary DNA (cDNA) target sequence using the Polymerase Chain Reaction (PCR). The method of the present invention is particularly suited to preparing a DNA or cDNA target sequence for sequencing purposes.

Background Art

PCR selectively amplifies a target sequence from a DNA template and consists essentially of three steps: denaturation of the DNA template; hybridization of primers to the target sequence or sequences flanking the target sequence; and extension of the primers by a DNA polymerase. Traditionally, the products of PCR (herein referred to as amplicons) are analysed by gel electrophoresis, a method which distinguishes DNA sequences according to their molecular weight. However many contemporary applications, such as massively parallel sequencing (also known as Next Generation Sequencing or NGS), require PCR amplicons to incorporate specific modifications, often in the form of functional sequences at their ends.

A number of methods for generating amplicons incorporating functional sequences exist, but all have disadvantages such as increased cost, complexity of processing, potential for cross-contamination, carry-over or a combination of these. For example, the conventional one-step PCR method involves adding functional sequences to the 5' end of the primers and then performing PCR in the normal way to add functional sequences to either end of the amplicon. However, this method is cumbersome and expensive, particularly when a large number of different functional sequences are required. Further, this method is not suitable for complex combinations or automated processing.

The conventional two-step PCR method is typically used to generate more complex constructs. In the conventional two-step PCR method, a primary PCR step is performed as described above to add 'universal sequences' to either end of the amplicon. The primers used in the primary PCR step comprise a 3' gene specific sequence, which is complimentary to DNA sequences flanking the target sequence, and a 5' universal sequence. A secondary PCR step is then performed using the amplicons generated in the primary PCR as the template. The primers used in the secondary PCR step are designed such that their 3' ends are complimentary to and hybridise to the universal sequences at the 5' ends of the amplicons from the primary PCR. The primers used in the secondary PCR step add the required functional sequences to the amplicon by virtue of an appropriate array of 5' tails. This method allows more complex combinations of functional sequences to be added to PCR amplicons using a relatively small set of primers.

The conventional two-step PCR method requires multiple steps and can therefore be cumbersome, particularly if automated liquid handling is not available and a large number of samples need to be analysed. In addition, the primary and secondary PCR steps are conducted separately, with the product of the primary PCR step being used as a template in the secondary PCR step. This necessitates open tubes and/or tube transfers. Accordingly, there is a real risk of cross-contamination or carry-over. Since PCR involves exponential amplification, even low levels of contamination can have very significant effects that are difficult to detect, particularly when the process is used as a preparation step for sensitive analysis like NGS.

Further, the secondary PCR step involves the use of 'universal primers', so called because they all comprise a sequence complimentary to the universal sequence of the primers used in the primary PCR step. In this way, any universal primer may hybridise to any target containing the appropriate universal sequence. This flexibility brings with it the increased risk of amplification and subsequent interrogation of an incorrect amplicon.

Two-step PCR methods are disclosed in WO 2007/130967, WO 03/097794, WO 2012/054933 and WO 02/14534.

Attempts have been made to simplify the conventional two-step PCR method by combining the primary and secondary PCR steps in a single reaction. Limited success has been achieved for low complexity constructs by optimising the relative primary and secondary primer concentrations and/or PCR reaction conditions. However, optimisation is time consuming and this method is not capable of robustly generating complex amplicon constructs such as those required for NGS.

BRIEF SUMMARY OF THE INVENTION

The present invention provides an improved method for generating amplicon constructs, particularly complex amplicon constructs. As opposed to the conventional two step PCR method discussed above, advantageously, the method of the present invention can be performed in a single closed tube PCR. Further, the method of the present invention is cheap and simple to use, increases targeting specificity, has the potential for multiplexing and significantly reduces the chances of amplifying illicit targets or appending incorrect functional sequences.

The present invention provides a method for generating amplicon constructs of a target sequence, the method comprising providing:

a target sequence;

an oligonucleotide probe, comprising a universal sequence and further comprising, at or towards its 5' end, a target specific sequence capable of hybridising to the reverse complement of a sequence at, or flanking one of the 3' ends of the target sequence;

a universal primer, comprising at its 3' end a sequence capable of hybridising to the universal sequence of the oligonucleotide probe; and performing a Polymerase Chain Reaction (PCR).

The present invention provides a method for generating amplicon constructs of a target sequence, using the Polymerase Chain Reaction (PCR). In a preferred embodiment, the amplicon constructs generated using the method of the present invention are tagged in that they incorporate one or more functional sequences and/or groups, which flank the amplified target sequence, at one or both ends. The functional sequences and/or groups impart physical and/or chemical properties on the amplicon constructs which can be exploited in a downstream process to further interrogate the target sequence. The method of the present invention is particularly suited to generating amplicon constructs which incorporate functional sequences suitable for sequencing, for example Next Generation Sequencing (NGS). Although it is to be appreciated that the method of the present invention can be used to generate amplicon constructs comprising any desired functional sequences suitable for other interrogatory purposes, including but not limited to forensics and the detection and the diagnosis of hereditary or infectious diseases.

As discussed above, the method of the present invention comprises providing a target sequence and amplifying the target sequence by PCR. Any form of PCR can be employed in the method of the present invention. For example, the traditional form of PCR used to amplify DNA, Reverse-Transcriptase PCR (RT-PCR), a PCR technique used to amplify expressed DNA, and Real-Time PCR (qPCR), a PCR technique used to quantitatively measure the amplification of DNA, are all forms of PCR which can be employed in the method of the present invention. Similarly any PCR thermal cycling operating conditions can be employed in the method of the present invention.

It is to be appreciated that in order to perform PCR on the target sequence additional reagents are required and that those reagents will vary depending on the type of PCR technique employed. For example, to perform PCR, the method of the present invention provides a heat stable DNA polymerase, (Taq polymerase) and all four deoxyribonucleotides (dATP, dTTP, dCTP, dGTP). Similarly, to perform RT-PCR, the enzyme reverse transcriptase is provided. However, as will be discussed in more detail below, the method of the present invention does not provide target-specific primers. Rather, target-specific primers are generated in situ by the method of the present invention.

As discussed above, the method of the present invention comprises providing a target sequence and amplifying the target sequence by PCR. The target sequence can be a DNA, cDNA or RNA sequence. If the method of the present invention is to provide a cDNA target sequence, the cDNA target sequence may be prepared, prior to use in the method of the present invention. The cDNA target sequence can be prepared from its corresponding RNA sequence using the enzymes reverse transcriptase and DNA polymerase in known manner. Alternatively, the cDNA sequence can be prepared from its corresponding RNA sequence in situ, in which case, the method of the present invention provides the corresponding RNA sequence and Reverse Transcriptase PCR (RT-PCR) is preferably performed.

The DNA, cDNA or RNA target sequence can be derived from any part of the genome of any organism. For example, the DNA, cDNA or RNA target sequence can be derived from the human genome or other animal genomes, plant genomes, fungal genomes, bacterial genomes, viral genomes and/or any other DNA molecule. It is to be appreciated that the DNA, cDNA or RNA sequence can be provided as a component part of a DNA vector, such as a plasmid or a virus. It is also to be appreciated that the DNA, cDNA or RNA target sequence can be provided as a sample of different DNA, cDNA or RNA target sequences or in isolated form. Furthermore, it is to be appreciated that the method of the present invention can be used to amplify one specific DNA, cDNA or RNA target sequence or several different DNA, cDNA or RNA target sequences at one time.

It is to be appreciated that the method of the present invention may be used to generate amplicon constructs of a plurality of different DNA, cDNA and/or RNA target sequences at the same time. In such circumstances multiplex PCR may be performed on the DNA, cDNA and/or RNA target sequences.

As discussed above, the method of the present invention comprises providing a DNA, cDNA or RNA target sequence and performing PCR. Accordingly, general references herein to "target sequence" in relation to the present invention are to include DNA, cDNA or RNA target sequences. In addition, general references herein to "PCR" in relation to the present invention are to include all types of PCR and operating conditions unless otherwise stated.

The method of the present invention comprises providing a target sequence, an oligonucleotide probe, a universal primer and performing the Polymerase Chain Reaction (PCR). As will be discussed in more detail below, the method of the present invention can be used to generate amplicon constructs of a target sequence, more preferably tagged amplicon constructs of a target sequence, in a single PCR, or one-step reaction. It is to be appreciated that a single PCR will typically comprise a series of cycles, with each cycle consisting of a series of defined thermal incubations.

The method of the present invention relies upon the in situ generation of target specific primers. Towards the beginning of the reaction, the universal primer hybridises to the oligonucleotide probe and is extended to generate a target-specific primer in situ. The target-specific primer may contain any required functional sequences by virtue of the functional sequences present in the universal primer (to be discussed in more detail below). The oligonucleotide probe is not depleted in this reaction and is therefore able to act catalytically and hybridise with other universal primers in subsequent rounds of thermal cycling during the PCR to form more target-specific primers. The target sequence is amplified by the target-specific primers, once formed, to create amplicon constructs flanked with sequences corresponding to those contained in the in situ generated target-specific primers. This method is advantageous in that it enables complex amplicon constructs to be formed in a single PCR.

The method of the present invention comprises providing a universal primer and an oligonucleotide probe which interact during PCR to form a target-specific primer. The oligonucleotide probe may be any nucleic acid sequence or combination of nucleic acid sequences. In a preferred embodiment, the oligonucleotide probe is a single stranded DNA sequence. Other embodiments could use oligonucleotide probes comprising entirely or in part, other types of nucleic acid, for example RNA or Linked Nucleic Acids (LNA™)

The oligonucleotide probe is not a target specific primer as it does not comprise, at its 3' end, a sequence complimentary to one of the 3' ends of the target sequence or a sequence flanking the 3' end of the target sequence. As a consequence, the probe cannot hybridise to the target sequence.

As discussed above, the oligonucleotide probe comprises, at or towards its 5' end, a target specific sequence capable of hybridising to the reverse complement of the sequence at, or flanking one of the 3' ends of the target sequence. Sequences disposed towards the 5' end of the oligonucleotide probe are to be interpreted as being disposed within the 5' end portion of the oligonucleotide probe.

The target specific sequence can be a sequence identical to the 3' end sequence of the target sequence or a sequence flanking one of the 3' ends of the target sequence. Alternatively, the target specific sequence can be a sequence substantially identical to the 3' end sequence of the target sequence or a sequence flanking one of the 3' ends of the target sequence such that the resulting target specific primer is able to hybridise to the target specific sequence or a sequence flanking the target specific sequence.

The oligonucleotide probe further comprises a universal sequence to enable hybridisation of the oligonucleotide probe to the universal primer. The universal sequence can be any sequence, so long as it is sufficiently complementary to a sequence located on the universal primer such that it can hybridise to the sequence located on the universal primer.

The universal sequence can be located anywhere on the oligonucleotide probe apart from at its 5' end. In particular, the universal sequence may be located at any position on the oligonucleotide probe between the 5' end up to and including the 3' end. In a preferred embodiment, the universal sequence is located at the 3' end of the oligonucleotide probe.

The oligonucleotide probe may comprise one or more additional sequences. Provided those additional sequences form part of, or the entire universal sequence, or are disposed 5' of the universal sequence and 3' of the target specific sequence, the reverse compliment of those additional sequences will be present in the resulting in situ generated target-specific primers. If additional sequences are present, one or more of those sequences can be functional sequences capable of imparting chemical and/or physical properties on the resulting target-specific primers. Any functional sequences can be employed. Suitable functional sequences include but are not limited to downstream oligonucleotide binding sites, restriction enzyme recognition sites, and reaction identification sequences.

In one embodiment, the 3' end of the oligonucleotide probe comprises a blocking group capable of blocking polymerase extension. In this way, the 3' end of the oligonucleotide probe cannot be extended by polymerase during PCR. Any blocking group suitable for blocking the 3' end of an oligonucleotide may be employed. Suitable blocking groups include but are not limited to dideoxynucleotide triphosphates (ddNTP's) and Spacer C3. These groups are known in the art and are commercially available. Experiments have been conducted to establish whether the presence of a blocking group is advantageous or essential to functionality and it has been found that it is not. However, a blocking group may prevent unwanted consequences incurred from the extension of the probe, for example cross hybridisation and/or interference. The results of these experiments are discussed in more detail in the Examples. Accordingly, it is preferred to employ a blocking group, thereby simplifying the structure of the oligonucleotide probe and avoiding any unwanted consequences of extension of the oligonucleotide probe. Extension of the oligonucleotide probe may also be prevented by designing the oligonucleotide probe such that it is not complimentary to the 3' end of the universal primer.

The length of the oligonucleotide probe is determined by the lengths of the universal sequence, the target specific sequence and any additional sequences present. Preferably, the lengths of the universal sequence and the target specific sequence are the minimum lengths required to confer sufficient specificity for hybridisation to the universal primer and the target sequence respectively. Additional length may result in unwanted cross hybridisation secondary structures and/or interference. In a preferred embodiment, the oligonucleotide probe comprises up to 100 nucleotides, more preferably up to 50 nucleotides, more preferably still between 20 and 50 nucleotides, yet still more preferably between 30 and 40 nucleotides.

As discussed above, in the method of the present invention, an oligonucleotide probe is provided. However, it is to be appreciated that two or more probes may be provided, these being specific to the same 3' end of the target sequence or the same sequence flanking one of the 3' ends of the target sequence. Alternatively, the two or more probes can be specific to different 3' ends of the target sequence or sequences flanking different 3' ends of the target sequence In one preferred embodiment, the method of the present invention provides a pair of first and second oligonucleotide probes. In this embodiment, the first oligonucleotide probe comprises a target specific sequence, specific to one of the 3' end sequences of the target sequence or a sequence flanking one of the 3' ends of the target sequence and the second oligonucleotide probe comprises a target specific sequence specific to the other 3' end sequence of the target sequence or a sequence flanking the other 3' end of the target sequence. In this way, a pair of first and second target specific primers is generated in situ, these being capable of adding functional sequences to both ends of the target sequence.

In embodiments where the method provides a pair of first and second oligonucleotide probes, the first and second oligonucleotide probes can comprise the same or different universal sequences. Preferably, the pair of first and second oligonucleotide probes comprise different universal sequences in order to independently append functional sequences to each end of the resulting amplicon. Similarly, the first and second oligonucleotide probes can comprise the same or different additional and/or functional sequences. Preferably, the first and second oligonucleotide probes comprise different additional sequences in order to increase the potential number of different amplicon constructs that can be formed from any one target sequence.

As discussed above, the method of the present invention comprises providing a universal primer and an oligonucleotide probe and performing PCR to create a target-specific primer capable of amplifying the target sequence. The universal primer hybridises to the universal sequence of the oligonucleotide probe and is extended during PCR by DNA polymerase using the 5' end of the oligonucleotide probe as the template, to form a target specific primer. The target specific primer is target specific since it comprises a 3' sequence sufficiently complimentary to one of the 3' ends of the target sequence or a sequence flanking the 3' end of the target sequence so as to allow suitable priming specificity.

The universal primer is a single stranded nucleic acid sequence. Any nucleic acid sequence or combination of nucleic acid sequences may be employed. In a preferred embodiment, the universal primer is a single stranded DNA sequence. Other embodiments could use universal primers comprising entirely or in part, other types of nucleic acid, for example RNA or Linked Nucleic Acids (LNA™).

The universal primer comprises, at its 3' end, a sequence capable of hybridising to the universal sequence of the oligonucleotide probe. To achieve this, the 3' end of the universal primer is complementary to the universal sequence of the oligonucleotide probe or sufficiently complementary to the universal sequence of the oligonucleotide probe to enable hybridisation. During PCR, the universal primer hybridises to the oligonucleotide probe and is extended, using the 5' end of the oligonucleotide probe as the template. The resulting 3' end of the in situ generated target specific primer is capable of hybridising to one of the 3' end sequences of the target sequence or a sequence flanking one of the 3' ends of the target sequence and of being extended by polymerase in further rounds of PCR.

In a preferred embodiment, the universal primer further comprises one or more functional sequences and/or groups, located at or towards its 5' end. As discussed above, functional sequences and/or groups disposed towards the 5' end of the universal primer are to be interpreted as being disposed within the 5' end portion of the universal primer. The functional sequences and/or groups impart chemical and/or physical properties on the resulting target-specific primer and amplicon constructs. Any functional sequences and/or groups can be used and these will vary depending upon the subsequent intended use of the resulting amplicons. The use of such functional sequences is known in the art.

For example, if the tagged amplicons are to be sequenced on an Illumina MiSeq® instrument, the universal primer preferably comprises a sample specific index sequence. This type of sequence is typically used during sequencing analysis to identify from which sample the amplicons were derived. The universal primer preferably further comprises an adaptor sequence, used to hybridise the amplicons to the sequence flow cell and perform an initial (clonal) amplification of the amplicon prior to sequencing. In addition, for this application, the universal sequence of the oligonucleotide probe is preferably complementary to the sequencing primers used for the paired end sequencing reads on the instrument.

Other types of functional sequences include, but are not limited to enzyme recognition sequences, sequences for sample identification and oligonucleotide binding sequences for use in downstream analysis applications. Functional groups on the universal primer include, but are not limited to, fluorescent labels and binding groups such as biotin.

The length of the universal primer is determined by the length of the universal sequence and any additional sequences present. In a preferred embodiment, the universal primer comprises up to 200 nucleotides, more preferably up to 150 nucleotides, more preferably still between 50 and 100 nucleotides, yet still more preferably between 70 and 100 nucleotides.

The method of the present invention may comprise providing two or more universal primers, these being capable of hybridising to a common oligonucleotide probe or to different oligonucleotide probes. In a preferred embodiment, a pair of first and second universal primers is provided; each comprising a sequence capable of hybridising to the universal sequence of the first and second oligonucleotide probes respectively. In embodiments where the method of the present invention provides a pair of first and second universal primers, the first and second universal primers preferably comprise different functional sequences and/or groups and/or combinations of these in order to independently append functional sequences and/or groups to each end of the resulting amplicon and increase the potential number of amplicon constructs that can be formed from any one target sequence.

In other embodiments of the method of the present invention, a plurality of different oligonucleotide probes or probe pairs and universal primers or primer pairs are provided to amplify multiple different target sequences in a single multiplex reaction.

The oligonucleotide probe and universal primer are employed at suitable concentration ratios. Suitable concentration ratios can be readily determined by routine experimentation. It has been found that it is preferable to provide the oligonucleotide probe at a lower concentration relative to the concentration of the universal primers.

Preferably, the ratio of the concentration of the universal primer to the concentration of the oligonucleotide probe is greater than 2:1, more preferably greater than 5:1, still more preferably greater than 10:1. In one preferred embodiment the ratio of the concentration of the universal primer to the concentration of the oligonucleotide probe may be up to 4000:1, more preferably up to 2000:1, still more preferably up to 1000:1, more preferably still up to 500:1.

In a preferred embodiment, the relative concentration of universal primer to oligonucleotide probe is from 10:1 to 300:1, more preferably still from 12:1 to 275:1, yet still more preferably from 15:1 to 265:1. A particularly preferred relative concentration of universal primer to oligonucleotide probe is from 16:1 to 256:1.

As discussed above, the method of the present invention can be used to generate amplicon constructs of a target sequence in a single PCR. Accordingly, there is no risk of PCR cross contamination from concurrent reactions. However, it is to be appreciated that the method of the present invention can also be used to generate amplicon constructs of a target sequence in two separate PCR steps. In the first PCR step, the target-specific primers are prepared from the oligonucleotide probes and universal primers. In the second PCR step, the target sequence is amplified by the target-specific primers generated by the first PCR step.

Accordingly, in a further aspect, the present invention provides a method for preparing a target-specific primer for use in generating amplicon constructs from a target sequence, the method comprising providing:

an oligonucleotide probe, comprising a universal sequence and further comprising at or towards its 5' end, a target specific sequence capable of hybridising to the reverse complement of a sequence at one of the 3' ends of the target sequence or the reverse complement of a sequence flanking one of the 3' ends of the target sequence;

a universal primer, comprising at its 3' end a sequence capable of hybridising to the universal sequence of the oligonucleotide probe; and performing a Polymerase Chain Reaction.

The oligonucleotide probe and universal primer and the conditions in which they interact during PCR to form the target-specific primer have been discussed in detail above, in relation to the first aspect of the present invention. Once formed according to the method of the further aspect of the present invention, the target-specific primer can be used to amplify a target sequence in a subsequent and separate PCR to generate amplicon constructs of that target sequence, preferably flanked with one or more functional sequences. As above, the target sequence can be a DNA, RNA or cDNA target sequence and can be derived from any part of the genome of any organism.

As above, it is to be appreciated that the method of this further aspect of the present invention can be used to prepare a pair of first and second target specific primers, capable of flanking the target sequence with functional sequences at one or both ends. To prepare a pair of first and second target-specific primers, a pair of first and second oligonucleotide probes and a pair of first and second universal primers are provided.

It is also to be appreciated that the method of this further aspect of the present invention can be used to prepare a plurality of target-specific primers, capable of hybridising to different target sequences or sequences flanking different target sequences. In this way, the method of the further aspect of the present invention can be employed to prepare a group of target specific primers for use in Multiplex PCR.

As discussed above, the method of the present invention can be employed to generate amplicon constructs of a DNA, cDNA or RNA target sequence. If the method is used to generate amplicon constructs of a cDNA target sequence, the cDNA sequence may be prepared from its corresponding RNA sequence in advance. Alternatively, the cDNA sequence may be formed in situ; in which case, an RNA sequence is provided and RT-PCR is performed. Once formed by reverse transcription, the cDNA hybridises to and is amplified by target-specific primers during PCR. The target specific primers are also formed in situ by PCR.

It is to be appreciated however that the method of the present invention can also be used to generate cDNA amplicon constructs directly from an RNA target sequence, the cDNA amplicon constructs comprising one or more functional sequences or groups at one or both ends, which may then be analysed or processed as required.

Accordingly, in a still further aspect, the present invention provides a method for generating cDNA amplicon constructs from an RNA target sequence, the method comprising providing:

a target-specific primer;
an RNA target sequence; and
performing Reverse Transcription;

wherein the target-specific primer is prepared according to a method as hereinbefore described.

The target-specific primer and how it can be formed from an oligonucleotide probe and a universal primer has been described in detail above in relation to the first aspect of the present invention. As above, the target-specific primer can be prepared by PCR in advance, prior to use in the method of this still further aspect of the present invention. Alternatively, the target-specific primer can be prepared in situ. If the target-specific primers are to be prepared in situ, the method of this still further aspect of the present invention further provides an oligonucleotide probe and a universal primer, and PCR is performed as discussed above in relation to the first aspect of the present invention. Once the target-specific primer has been formed by PCR, the reverse transcription reaction can be carried out on the RNA target sequence. In practice, the PCR reaction and reverse transcription reaction can occur in parallel.

The RNA target sequence provided in the method of the present invention can come from any part of the genome of any organism, including the human genome or other animal genomes, plant genomes, fungal genomes, bacterial genomes, viral genomes and/or any other RNA molecule. As above, it is to be appreciated that the RNA target sequence can be provided as a sample of different RNA target sequences or in isolated form. Furthermore, it is to be appreciated that the method of the present invention can be used to amplify one specific RNA target sequence or several different RNA target sequences at one time.

As above, the method of this still further aspect of the present invention requires performing reverse transcription on the RNA target sequence. Accordingly, it is to be appreciated that additional reagents necessary for the reverse transcription reaction, such as the enzyme reverse transcriptase, are necessary.

In use, the target-specific primers bind to the RNA target sequence and are extended by the reverse transcriptase enzyme during the reverse transcription reaction. The resulting cDNA may be further amplified by PCR.

In a yet still further aspect, the present invention provides an oligonucleotide probe for use in preparing a DNA, cDNA or RNA target-specific primer, the oligonucleotide probe comprising a universal sequence and further comprising at or towards its 5' end, a target-specific sequence capable of hybridising to the reverse complement of a sequence at one of the 3' ends of a DNA, cDNA or RNA target sequence or the reverse complement of a sequence flanking one of the 3' ends of the DNA, cDNA or RNA target sequence.

The constituent parts of the oligonucleotide probe, including the target specific sequence and the universal sequence have been discussed in detail above, in relation to the first aspect of the present invention.

BRIEF DESCRIPTION OF THE SEVERAL VIEWS OF THE DRAWINGS

FIG. 3 shows the first and second target specific primers (SEQ ID NOS 11 TO 16) produced in the reaction of FIG. 2;

DETAILED DESCRIPTION OF THE INVENTION

Embodiments of the present invention will now be described for illustration purposes only, by way of the following examples.

Example 1

The method of the present invention was performed to generate tagged amplicon constructs of a DNA target sequence for sequencing on an Illumina MiSeq® instrument. The target sequence for this assay is part of exon 7 of the human MUTYH gene (refSeq NM_001128425). The assay is used to analyse a specific mutation (MUTYH: c.536A>G, p.Tyr179Cys) known to cause MUTYH-associated polyposis (MAP).

A pair of first and second oligonucleotide probes were designed to the target sequence together with a pair of first and second universal primers. The target sequence, first and second oligonucleotide probes and first and second universal primers employed are shown in FIG. 1.

Figure 1:
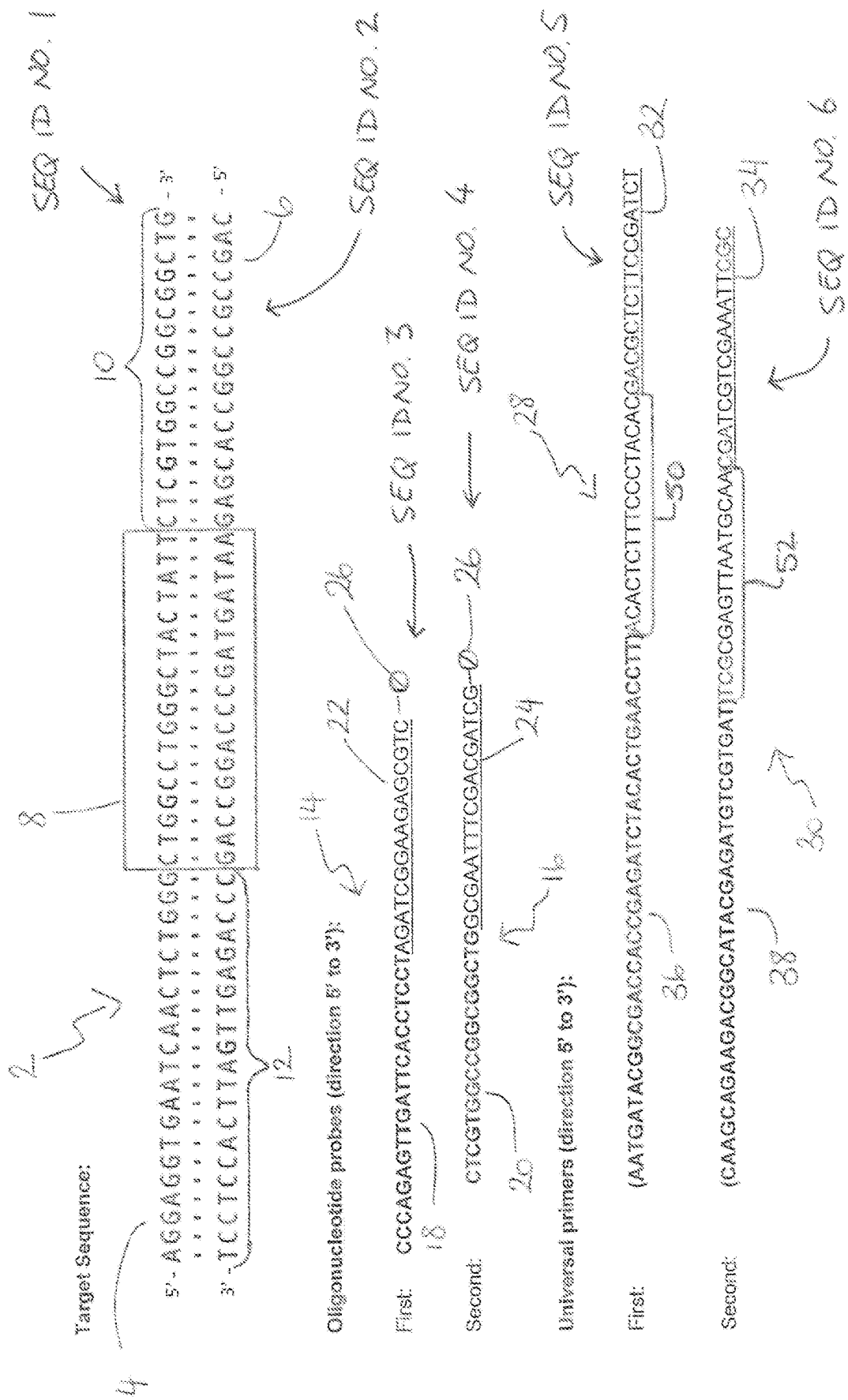
FIG. 1 shows a target sequence consisting of part of exon 7 of the human MUTYH gene (refSeq NM_001128425) (SEQ ID NOS 1 AND 2), together with a pair of first and second oligonucleotide probes (SEQ ID NOS 3 AND 4) and a pair of first and second universal primers (SEQ ID NOS 5 AND 6) according to an embodiment of the present invention.

Referring to FIG. 1, a DNA sequence is generally indicated as 2. As shown, the DNA sequence is double stranded and comprises a sense strand 4 and a complimentary antisense strand 6; the sense and antisense strands 4 and 6 running in opposite directions to each other. The DNA sequence 2 further comprises a target sequence 8 for amplification according to the method of the present invention. Sequences 10 and 12 flank the target sequence at the 3' end of the sense strand 4 and antisense strand 6 respectively.

The first oligonucleotide probe and second oligonucleotide probe are generally indicated as 14 and 16 respectively. As shown, the first and second oligonucleotide probes 14 and 16 are single stranded DNA sequences, each comprising a target specific sequence capable of hybridising to the reverse complement of one of the 3' ends of the target sequence 2 or a sequence flanking one of the 3' ends of the target sequence 2. In particular, the first oligonucleotide probe 14 comprises a sequence 18 which is identical to the sequence 12 of the antisense strand 6 of the target sequence 2. Similarly, the second oligonucleotide probe 16 comprises a sequence 20 which is identical to the sequence 10 of the sense strand 4 of the target sequence 2. The oligonucleotide probe sequences 18 and 20 are highlighted in bold.

As will be discussed in more detail below, the first and second oligonucleotide probes 14 and 16 further comprise a universal sequence 22 and 24 to facilitate hybridisation to the first and second universal primers 28 and 30 respectively. The universal sequences 22 and 24 are underlined.

The first and second oligonucleotide probes 14, 16 further comprise a blocking group 26, at their 3' end for blocking polymerase extension during PCR.

As shown, the first universal primer 28 and second universal primer 30 are single stranded DNA sequences. The first universal primer 28 comprises at its 3' end, a sequence 32, complimentary to the universal sequence 22 of the first oligonucleotide probe 14. Similarly, the second universal primer 30 comprises at its 3' end, a sequence 34, complimentary to the universal sequence 24 of the second oligonucleotide probe 16. The sequences 32 and 34 are underlined.

The first and second universal primers 28 and 30 each comprise, at their 5' end, functional sequences 36 and 38 respectively. The functional sequences 36 and 38 are variable and can be changed to suit the method under which the resulting tagged amplicons will be modified and/or analysed. For sequencing on an Illumina MiSeq® instrument, an amplicon of a target sequence must be flanked with a combination of different functional sequences at both ends. Those sequences can be selected from a library of different sequences designed by Illumina® for use on Illumina sequencing instruments such as MiSeq®. In particular, sequencing adaptor P5 can be used in combination with one of 8 sample specific index sequences (A501-A507). In addition sequencing adaptor P7 can be used in combination with one of 12 sample specific index sequences (A701-A712). Sequencing adaptors are used for flow cell hybridisation and bridge amplification and sample specific index sequences are used to identify from which sample the sequencing reads were derived.

In Example 1, functional sequence 36 comprises the P5 sequencing adaptor in combination with the sample specific index sequence A501. In addition, functional sequence 38 comprises the P7 sequencing adaptor in combination with the sample specific index sequence A701.

The first and second universal primers 28 and 30 further comprise, towards their 5' end, functional sequences 50 and 52 respectively. Functional sequences 50 and 52 are also variable and can be changed to suit the method under which the resulting tagged amplicons will be modified and/or analysed. For sequencing on an Illumina MiSeq® instrument, an amplicon of a target sequence must be flanked with sequencing primer binding sites S1 and S2 at both ends. Sequencing primer binding sites are used during sequencing to hybridise primers for the different sequencing reads.

In Example 1, functional sequence 50 comprises sequencing primer binding site S1 and the functional sequence 52 comprises sequencing primer binding site S2.

Figure 2:
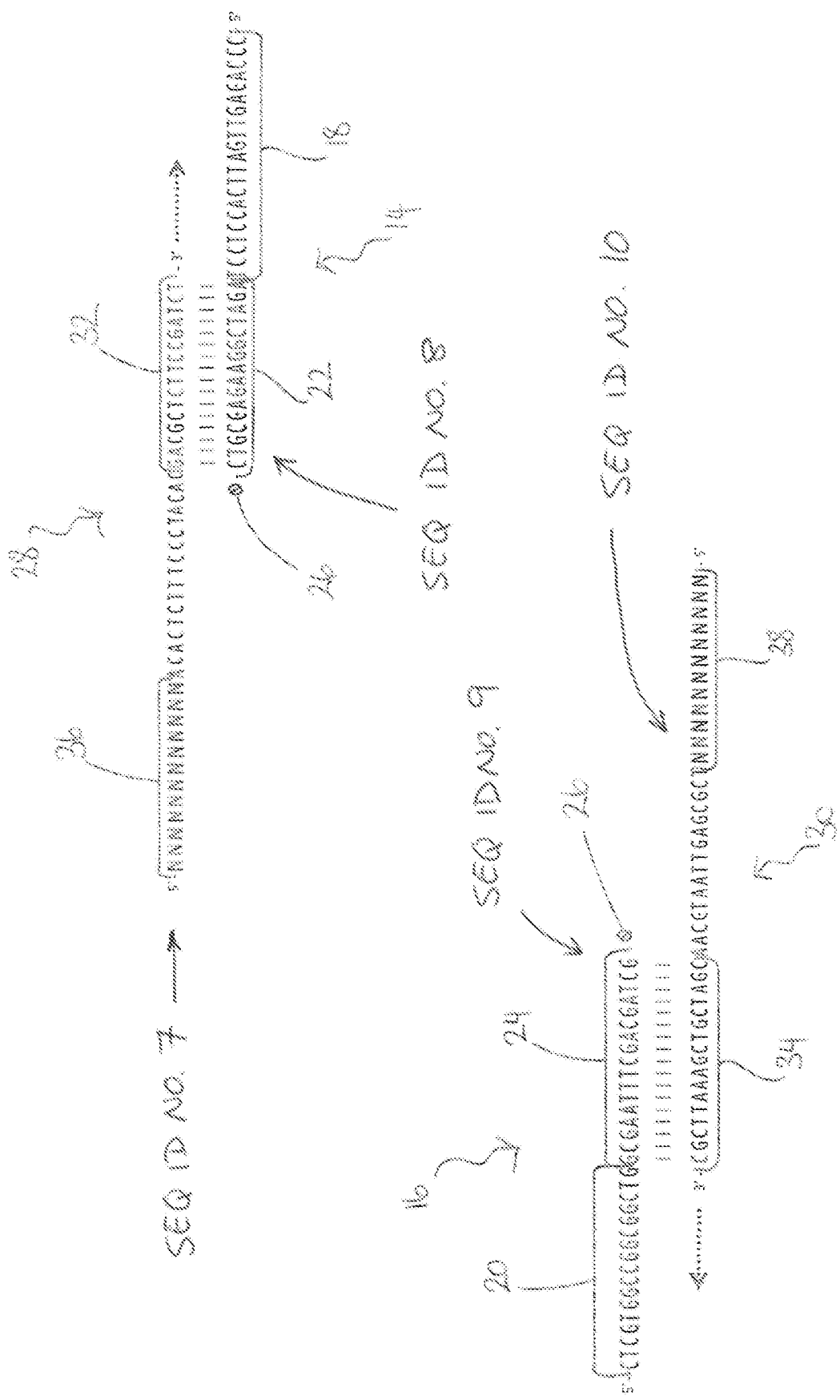
FIG. 2 shows the first reaction of the oligonucleotide probes (SEQ ID NOS 7 AND 9) and universal primers (SEQ ID NOS 8 AND 10) of FIG. 1.
Figure 4A:
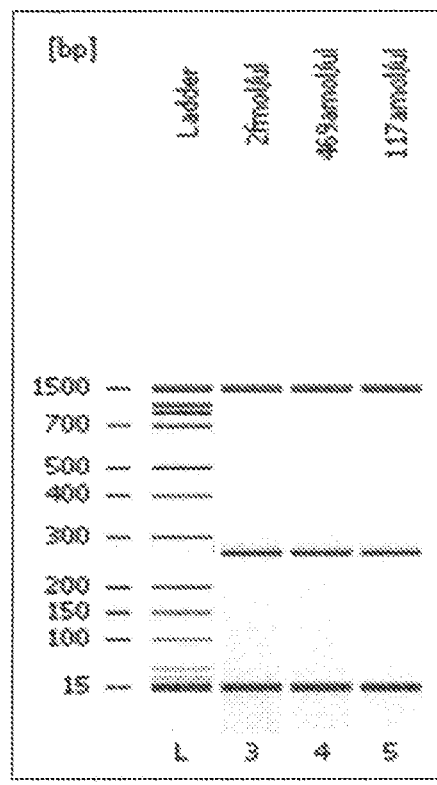
FIGS. 4a to 4d show the results of gel electrophoresis on DNA fragments obtained from different DNA target sequences according to the method of the present invention.
Figure 4B:
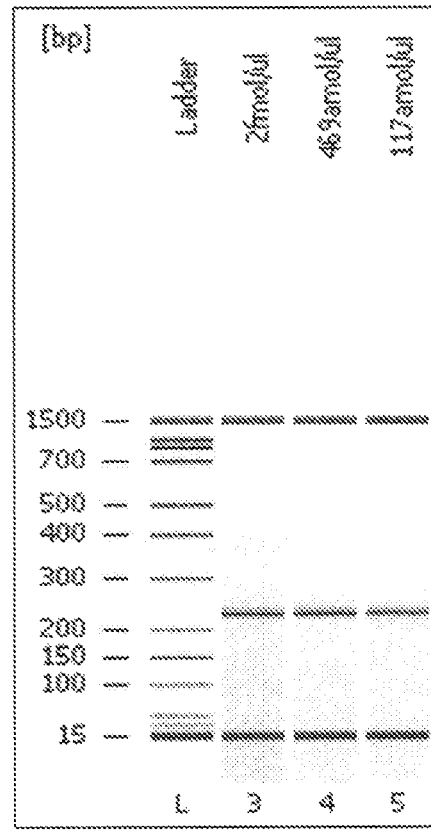
Figure 4C:
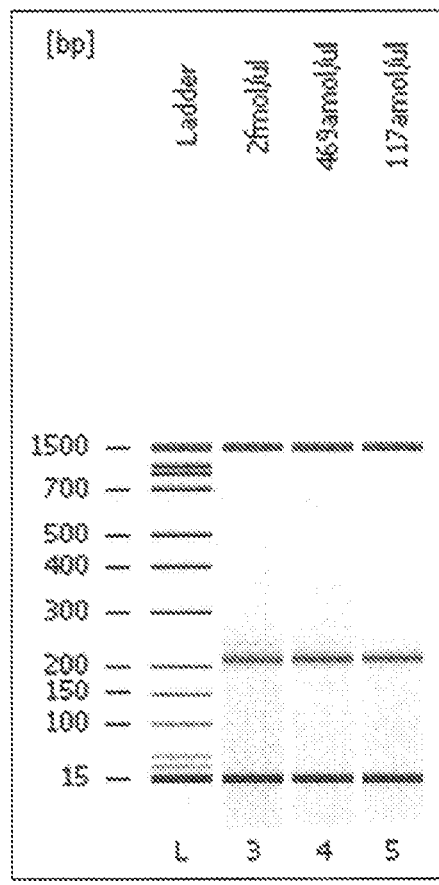
Figure 4D:
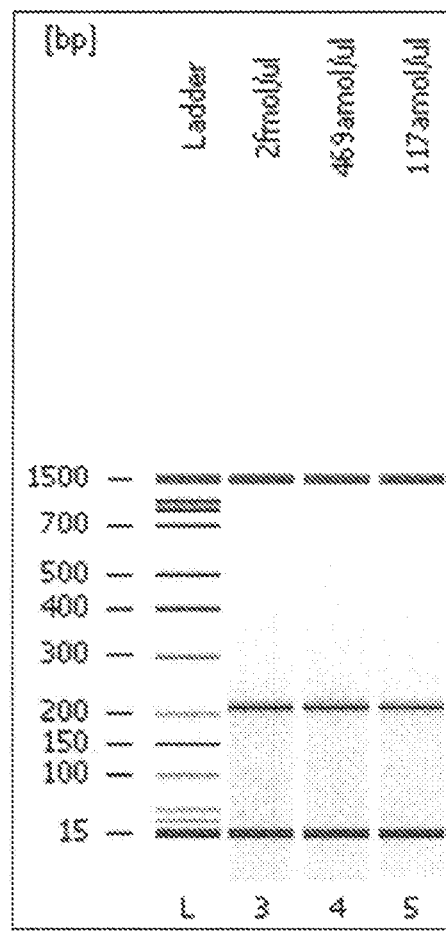

As previously discussed, the method of the present invention is capable of generating tagged amplicon constructs of a target sequence in a single PCR reaction sequence. The reaction sequence consists of two reactions; the first being the reaction between the first and second oligonucleotide probes 14 and 16 and the first and second universal primers 28 and 30 to produce first and second target specific primers and the second reaction being the reaction between the first and second target specific primers and the target sequence or sequences immediately flanking the target sequence to produce tagged amplicon constructs of the target sequence. Once the products from the first reaction are formed they are immediately available for use as components of the second reaction. As a consequence, the first and second reactions occur simultaneously. The first and second reactions of the single reaction sequence are illustrated in FIGS. 2 and 3 respectively.

The method of the present invention was carried out using a Q5® Hot Start High-Fidelity 2× Master Mix (New England Biolabs, product code: M0494L) and genomic DNA at a final concentration of 2 ng/ul in order to amplify exon 7 of the human MUTYH gene (refSeq NM_001128425) The reactions were thermal cycled as follows:
Step 1: 98° C. for 30 seconds
Step 2: 40 cycles of:
  98° C. for 10 seconds
  60° C. for 20 seconds
  72° C. for 20 seconds
Step 3: 72° C. for 5 minutes FIG. 2 illustrates the first reaction of the reaction sequence. For simplicity, the functional sequences 36 and 38 of the first and second universal primers 28 and 30 have been replaced with the letter "N".

As shown, the universal sequences 22 and 24 of the first and second oligonucleotide probes 14 and 16 hybridise to sequences 32 and 34 of the first and second universal primers 28 and 30 respectively. During PCR, the universal primers 28 and 30 are extended in the direction shown, by DNA polymerase using sequences 18 and 20 as template.

Figure 3:
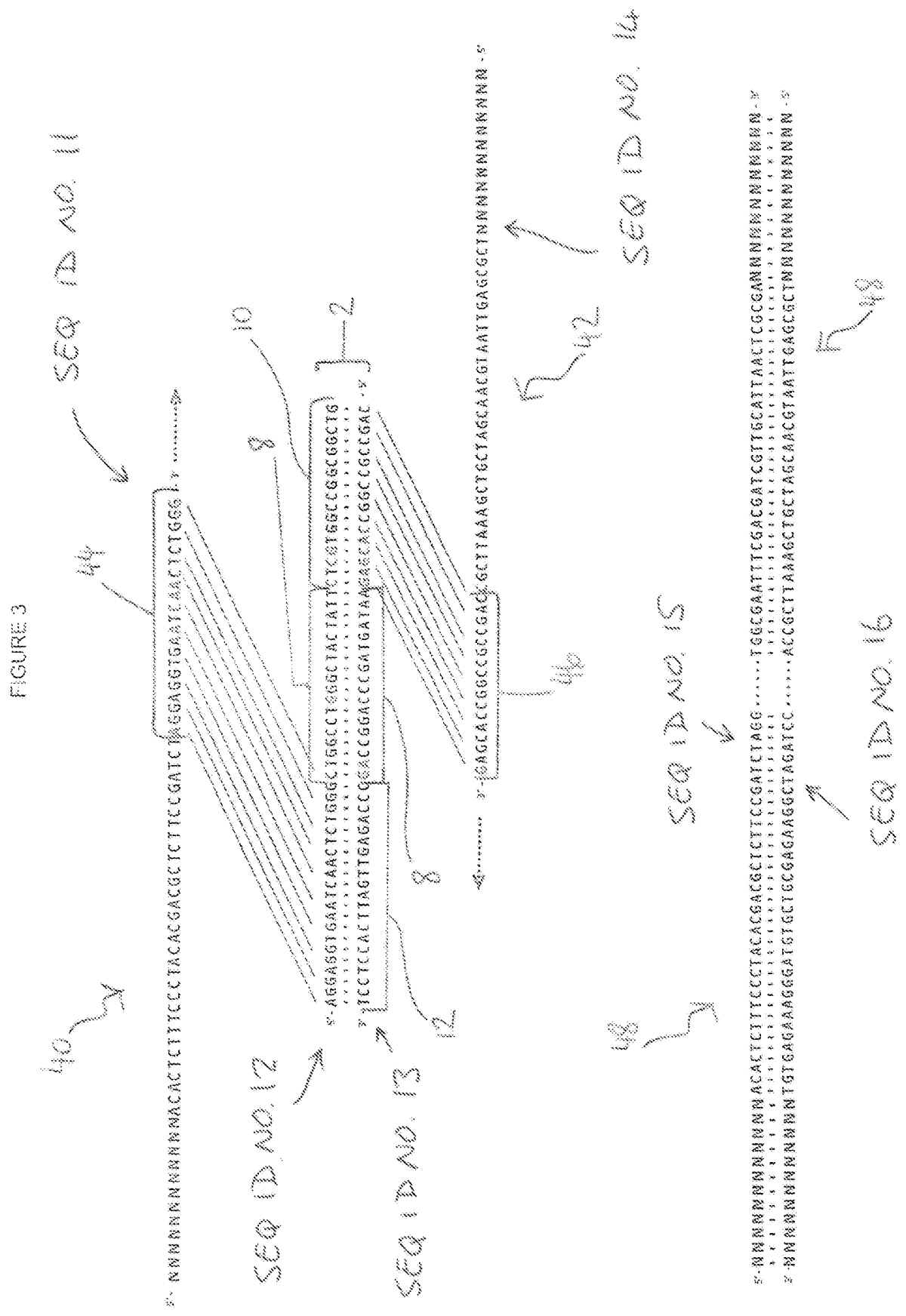

The resulting first and second target specific primers 40 and 42 are shown in FIG. 3. The target specific primers 40 and 42 comprise a 3' sequence 44 and 46 respectively, complimentary to 3' sequences 12 and 10 of the DNA sequence 2. Accordingly, the first and second target specific primers 40 and 42 are capable of hybridising to sequences 12 and 10 respectively of the DNA sequence 2. During PCR, the first and second target specific primers 40 and 42 are extended by DNA polymerase, using the target sequence 8 as template. In this way, the target sequence is amplified and the resulting amplicon constructs are tagged at both ends with sequences originating from the non target specific primers 28 and 30.

The resulting tagged amplicon constructs are generally indicated as 48. For simplicity, the entire amplicon sequence is not shown. Those sequences which are not shown are represented by dotted lines.

The amplicon constructs 48 were sequenced on an Illumina MiSeq® system to confirm that the correct target sequence was amplified. The amplicon constructs 48 corresponded to the correct target sequence.

Example 2

FIGS. 4a to 4d show the results of gel electrophoresis on DNA fragments obtained from different DNA target sequences according to the method of the present invention.

As discussed above, during PCR the universal primers and oligonucleotide probes interact to form the target-specific primers, which in turn are capable of amplifying the target sequence. An experiment was conducted to determine the optimum concentration ratio of oligonucleotide probe to target-specific primer.

Four pairs of first and second oligonucleotide probes were designed to 4 different DNA target sequences derived from the human genome, (referred to herein as target sequences W, X, T and U). A single pair of first and second universal primers were designed to be capable of hybridising to the 4 pairs of first and second oligonucleotide probes.

The target sequences W, X, T and U were sections of genes from the human genome as follows:
W: Exon 2 of the NRAS gene (refseq NM_002524.4)
X: Exon 3 of the NRAS gene (refseq NM_002524.4)
T: Exon 3 of the KRAS gene (refseq NM_004985.3)
U: Exon 2 of the KRAS gene (refseq NM_004985.3)

The method of the present invention was repeated several times on each target sequence, at a range of concentration ratios. Each time, the concentration of the universal primer was kept constant but the concentration of the oligonucleotide probes was decreased.

The method of the present invention was carried out using Hot Start High-Fidelity 2× Master Mix® (New England Biolabs, product code: M0494L) and human genomic DNA at a final concentration of 2 ng/ul. The reactions were thermal cycled as follows:
Step 1: 98° C. for 30 seconds
Step 2: 40 cycles of:
  98° C. for 10 seconds
  60° C. for 20 seconds
  72° C. for 20 seconds
Step 3: 72° C. for 5 minutes The amplicon constructs generated from each of the reactions for each target sequence were resolved using an Agilent Bioanalyzer DNA 1000 Kit. To establish whether the target sequences had been successfully amplified by the method of the present invention, the amplicons' expected lengths in base pairs were extrapolated against the visible bands of DNA. It was found that a higher concentration of the required amplicon construct was obtained where the concentration of the oligonucleotide probe was in the range of from 2 fmol/ul to 117 amol/ul and the concentration of the universal primer was 30 fmol/ul. This equates to an optimum concentration ratio of universal primer to oligonucleotide probe of between 16:1 to 256:1. The results for those reactions in which the optimum concentration ratio of universal primer to oligonucleotide probe was used are shown in FIGS. 4a to 4d.

As shown in FIGS. 4a to 4d, amplicon constructs of target sequences W, X, T and U were successfully formed by the method of the present invention when the concentration of the oligonucleotide probe was in the range of from 2 fmol/ul to 117 amol/ul and the concentration of the universal primer was 30 fmol/ul.

Example 3

Figure 5:
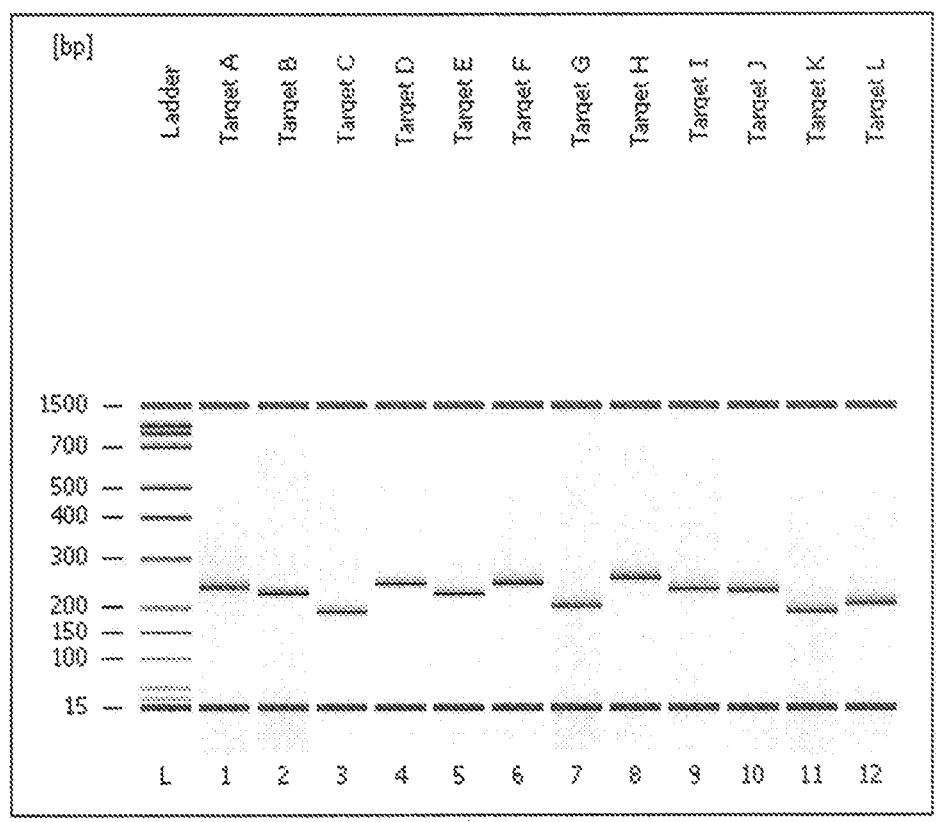
FIG. 5 shows the results of gel electrophoresis on DNA fragments obtained from different DNA target sequences according to the method of the present invention.
Figure 6:
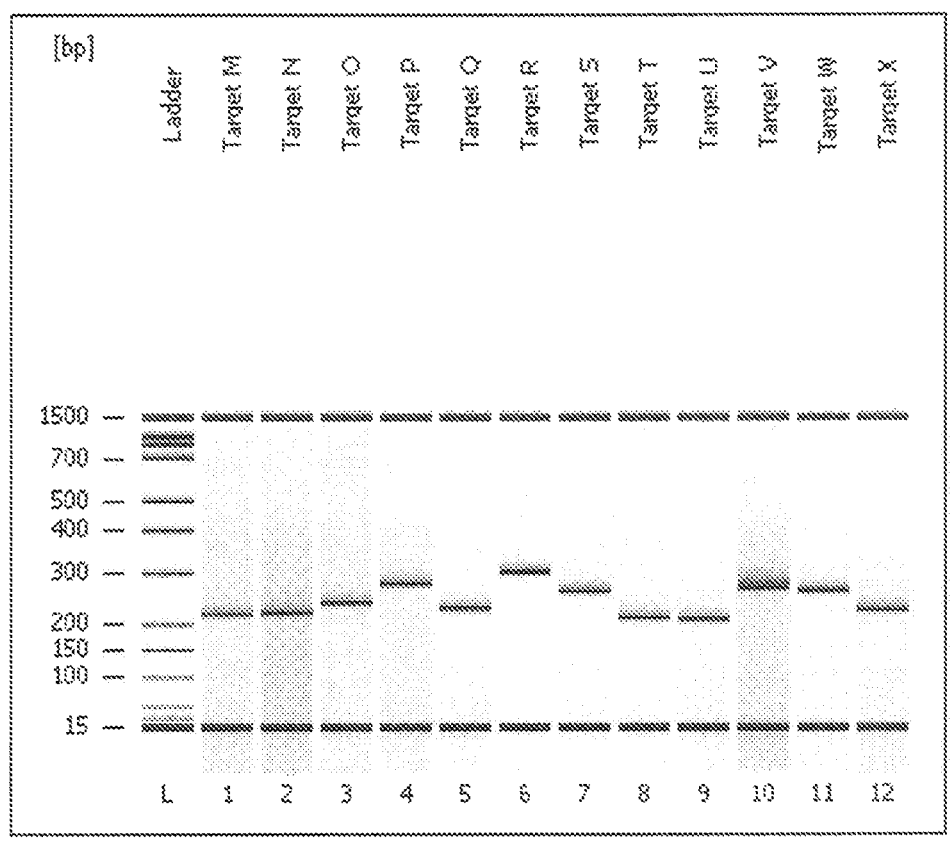
FIG. 6 shows the results of gel electrophoresis on DNA fragments obtained from different DNA target sequences according to the method of the present invention.

FIGS. 5 to 6 show the results of gel electrophoresis on DNA fragments obtained from different DNA target sequences according to the method of the present invention.

A further 20 pairs of first and second oligonucleotide probes were designed to a further 20 DNA target sequences (herein referred to as sequences A to S and V). As above, a single pair of first and second universal primers was designed to be capable of hybridising to the 20 pairs of first and second oligonucleotide probes.

The method of the present invention was performed on all 24 target sequences (sequences W, X, T and U from Example 2 and sequences A to S and V from Example 3), using a concentration ratio falling within the optimum concentration ratio obtained from Example 2 (concentration of universal primer: 30 fmol/ul and concentration of oligonucleotide probe: 1 fmol/ul).

All oligonucleotide probe pairs comprised a blocking group at their 3' end.

The method of the present invention was carried out using a Q5 ® Hot Start High-Fidelity 2× Master Mix (New England Biolabs, product code: M0494L) and human genomic DNA at a final concentration of 2 ng/ul. The reactions were thermal cycled as follows:
Step 1: 98° C. for 30 seconds
Step 2: 40 cycles of:
  98° C. for 10 seconds
  60° C. for 20 seconds
  72° C. for 20 seconds
Step 3: 72° C. for 5 minutes As above, the amplicon constructs generated were resolved using an Agilent Bioanalyzer DNA 1000 Kit and their expected size in base pairs extrapolated against the visible bands of DNA of known size. The approximate genomic location and expected size in base pairs for each of the amplicon constructs were as follows:

| Target | Gene | Exon | RefSeq | Expected size (bp) |
| --- | --- | --- | --- | --- |
| A | HFE | 2 | NM_000410 | 241 |
| B | HFE | 4 | NM_000410 | 220 |
| C | MUTYH | 7 | NM_001128425 | 191 |
| D | MUTYH | 13 | NM_001128425 | 249 |
| E | FGFR3 | 7 | NM_000142 | 222 |
| F | FGFR3 | 9 | NM_000142 | 243 |
| G | FGFR3 | 12 | NM_000142 | 201 |
| H | FGFR3 | 14 | NM_000142 | 261 |
| I | FGFR3 | 18 | NM_000142 | 229 |
| J | F2 | 14 | NM_000506 | 242 |
| K | F5 | 10 | NM_000130 | 194 |
| L | SERPINA1 | 5 | NM_000295 | 210 |
| M | SERPINA1 | 3 | NM_000295 | 219 |
| N | JAK2 | 14 | NM_004972 | 218 |
| O | BRAF | 15 | NM_004333 | 243 |
| P | EGFR | 18 | NM_005228 | 275 |
| Q | EGFR | 19 | NM_005228 | 233 |
| R | EGFR | 20 | NM_005228 | 293 |
| S | EGFR | 21 | NM_005228 | 263 |
| T | KRAS | 3 | NM_004985 | 206 |
| U | KRAS | 2 | NM_004985 | 209 |
| V | NPM1 | 11 | NM_002520 | 285 |
| W | NRAS | 2 | NM_002524 | 269 |
| X | NRAS | 3 | NM_002524 | 225 |

As shown, amplicon constructs of target sequences A to X were successfully formed by the method of the present invention when the optimum concentration ratio obtained from Example 2 was used (concentration of universal primer: 30 fmol/ul and concentration of oligonucleotide probe: 1 fmol/ul).

Example 4

Figure 7:
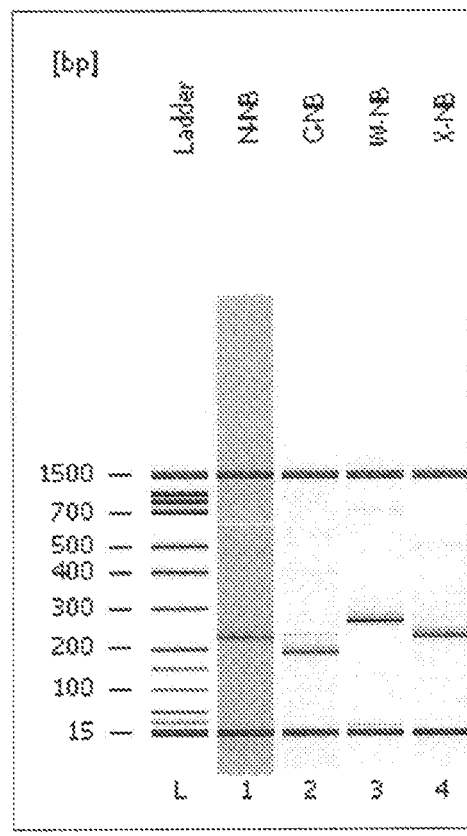
FIG. 7 shows the results of gel electrophoresis on DNA fragments obtained from different DNA target sequences according to the method of the present invention.

FIG. 7 shows the results of gel electrophoresis on DNA fragments obtained from different DNA target sequences according to the method of the present invention.

A further 4 pairs of first and second oligonucleotide probes were designed to a further 4 DNA target sequences (referred to herein as sequences C-NB, N-NB, W-NB and X-NB).

C-NB: Exon 14 of the JAK2 gene (refseq NM_004972.3)
N-NB: Exon 7 of the MUTYH gene (refseq NM_001128428)
W-NB: Exon 2 of the NRAS gene (refseq NM_002524.4)
X-NB: Exon 3 of the NRAS gene (refseq NM_002524.4)

Again, a single pair of first and second universal primers was designed to be capable of hybridising to the 4 pairs of first and second oligonucleotide probes. The method of the present invention was performed on all 4 target sequences using the optimum concentration ratio obtained from Example 2 (concentration of universal primer: 30 fmol/ul and concentration of oligonucleotide probe: 1 fmol/ul).

The 4 pairs of oligonucleotide probes were designed without a blocking group to determine if this affected the performance of the method of the present invention.

The method of the present invention was carried out using a Q5 ® Hot Start High-Fidelity 2× Master Mix (New England Biolabs, product code: M0494L) and human genomic DNA at a final concentration of 2 ng/ul. The reactions were thermal cycled as follows:
Step 1: 98° C. for 30 seconds
Step 2: 40 cycles of:
 98° C. for 10 seconds
 60° C. for 20 seconds
 72° C. for 20 seconds
Step 3: 72° C. for 5 minutes As above, the amplicon constructs generated were resolved using an Agilent Bioanalyzer DNA 1000 Kit and their expected size in base pairs extrapolated against the visible bands of DNA of known size. The expected size in base pairs for each of the amplicon constructs were as follows:

| Target | Expected size (bp) |
|---|---|
| C-NB | 191 |
| N-NB | 218 |
| W-NB | 269 |
| X-NB | 225 |

As shown, amplicon constructs of target sequences C-NB, N-NB, W-NB and X-NB were successfully formed by the method of the present invention when the optimum concentration ratio obtained from Example 2 was used (concentration of universal primer: 30 fmol/ul and concentration of oligonucleotide probe: 1 fmol/ul).

All 4 amplicon constructs generated were sequenced on an Illumina MiSeq® system to confirm that the correct target sequences were amplified. All 4 of the amplicon constructs corresponded to the correct target sequences. Accordingly, the presence or absence of the blocking group does not affect the performance of the method.

REFERENCE TO SEQUENCE LISTING SUBMITTED ELECTRONICALLY VIA EFS-WEB

The content of the electronically submitted sequence listing (Name: Sequence Listing.txt) on Apr. 18, 2019 is incorporated herein by reference in its entirety.

The invention claimed is:

1. A method for generating amplicon constructs of a target sequence, the method comprising providing
a double stranded target sequence, the target sequence having a first 3' end on its first nucleic acid strand and a second 3' end on its second nucleic acid strand, wherein the second nucleic acid strand is complementary to the first nucleic acid strand;
a first oligonucleotide probe and a second oligonucleotide probe, each of the first oligonucleotide probe and the second oligonucleotide probe comprising a universal sequence, wherein the universal sequence is located at the 3' end of each of the first oligonucleotide probe and the second oligonucleotide probe, and the first oligonucleotide probe further comprising, at its 5' end, a target specific sequence capable of hybridising to a complementary sequence on the first strand of the double stranded target sequence, the second oligonucleotide probe further comprising, at its 5' end, a target specific sequence capable of hybridising to a complementary sequence on the second strand of the double stranded target sequence;
a first universal primer and a second universal primer, the first universal primer comprising, at its 3' end, a sequence capable of hybridising to the universal sequence of the first oligonucleotide probe, and the second universal primer comprising, at its 3' end, a sequence capable of hybridising to the universal sequence of the second oligonucleotide probe; and
producing a first target-specific primer and a second target-specific primer by a polymerase extension reaction in the presence of the first oligonucleotide probe, the second oligonucleotide probe, the first universal primer, and the second universal primer, during the polymerase extension reaction, the first universal primer hybridises to the first oligonucleotide probe and is extended to form the first target-specific primer, and the second universal primer hybridises to the second oligonucleotide probe and is extended to form the second target-specific primer; and generating the amplicon constructs of the target sequence by a Polymerase Chain Reaction (PCR) in the presence of the double stranded target sequence, the first target-specific primer, and the second target-specific primer, during the PCR, the double stranded target sequence is amplified by hybridisation of the first target-specific primer to a sequence at the 3' end of the second nucleic acid strand of the double stranded target sequence and extension of the first target-specific primer and by hybridisation of the second target-specific primer to a sequence at the 3' end of the first nucleic acid strand of the double stranded target sequence and extension of the second target-specific primer.

2. The method according to claim 1, wherein the double stranded target sequence comprises a cDNA target sequence, the cDNA target sequence being formed in situ by reverse transcription of an RNA sequence complementary to the cDNA target sequence.

3. The method according to claim 1, wherein the target specific sequence of the first oligonucleotide probe is identical to a sequence at the 3' end of the second nucleic acid strand of the double stranded target sequence and the target specific sequence of the second oligonucleotide probe is identical to a sequence at the 3' end of the first nucleic acid strand of the double stranded target sequence.

4. The method according to claim 1, wherein each of the first oligonucleotide probe and the second oligonucleotide probe comprises one or more additional sequences; wherein the one or more additional sequences are located on 5' of the universal sequence and/or 3' of the target specific sequence; wherein the one or more additional sequences are functional sequences selected from sequences comprising downstream oligonucleotide binding sites, sequences comprising restriction enzyme recognition sites, and reaction identification sequences.

5. The method according to claim 1, wherein the 3' end of each of the first oligonucleotide probe and the second oligonucleotide probe comprises a blocking group capable of blocking a polymerase extension reaction.

6. The method according to claim 1, wherein each of the first universal primer and the second universal primer comprises one or more functional sequences and/or groups at its 5' end or in its 5' end portion; wherein the one or more functional sequences are selected from sequences comprising downstream oligonucleotide binding sites, sequences comprising restriction enzyme recognition sites, and reaction identification sequences and/or wherein the one or more groups are selected from fluorescent labels and binding groups.

7. The method according to claim 1, wherein each of the first oligonucleotide probe and the second oligonucleotide probe is provided at a lower concentration relative to the concentration of each of the first universal primer and the second universal primer; wherein the ratio of the concentration of each of the first universal primer and the second universal primer to the concentration of each of the first oligonucleotide probe and the second oligonucleotide probe is 12:1 to 275:1.

8. The method according to claim 1, wherein the method is performed in a one-step reaction.

9. The method according to claim 8, wherein the method is performed in a single closed tube.

10. The method according to claim 1, wherein the double stranded target sequence is generated from a single stranded cDNA.

11. The method according to claim 1, wherein the double stranded target sequence is two nucleic acid strands generated from a single stranded nucleic acid.

12. A method for preparing a first target-specific primer and a second target-specific primer for use in generating amplicon constructs from a double stranded target sequence, the double stranded target sequence having a first 3' end on its first nucleic acid strand and a second 3' end on its second nucleic acid strand, wherein the second nucleic acid strand is complementary to the first nucleic acid strand, the method comprising providing:

a first oligonucleotide probe and a second oligonucleotide probe, each of the first oligonucleotide probe and the second oligonucleotide probe comprising a universal sequence, wherein the universal sequence of the first oligonucleotide probe is located at its 3' end and the universal sequence of the second oligonucleotide probe is located at its 3' end; the first oligonucleotide probe further comprising, at its 5' end, a target specific sequence capable of hybridising to a complementary sequence on the first strand of the double stranded target sequence, and the second oligonucleotide probe further comprising, at its 5' end, a target specific sequence capable of hybridising to a complementary sequence on the second strand of the double stranded target sequence, wherein the 3' end of each of the first oligonucleotide probe and the second oligonucleotide probe comprises a blocking group capable of blocking a polymerase extension reaction, and wherein the blocking group is a dideoxynucleotide triphosphate (ddNTP) or a commercially available Spacer C3;

a first universal primer and a second universal primer, the first universal primer comprising, at its 3' end, a sequence capable of hybridising to the universal sequence of the first oligonucleotide probe and the second universal primer comprising, at its 3' end, a sequence capable of hybridising to the universal sequence of the second oligonucleotide probe; and preparing the first target-specific primer and the second target-specific primer by a polymerase extension reaction in the presence of the first oligonucleotide probe, the second oligonucleotide probe, the first universal primer, and the second universal primer, during the polymerase extension reaction, the first universal primer hybridises to the first oligonucleotide probe and is extended to form the first target-specific primer, and the second universal primer hybridises to the second oligonucleotide probe and is extended to form the second target-specific primer;

wherein each of the first oligonucleotide probe and the second oligonucleotide probe is provided at a lower concentration relative to the concentration of each of the first universal primer and the second universal primer; wherein the ratio of the concentration of each of the first universal primer and the second universal primer to the concentration of each of the first oligonucleotide probe and the second oligonucleotide probe is 10:1 to 500:1.

13. The method according to claim 12, wherein each of the first oligonucleotide probe and the second oligonucleotide probe comprises one or more additional sequences; wherein the one or more additional sequences are located on 5' of the universal sequence and/or 3' of the target specific sequence; wherein the one or more additional sequences are functional sequences selected from sequences comprising downstream oligonucleotide binding sites, sequences comprising restriction enzyme recognition sites, and reaction identification sequences.

14. The method according to claim 12, wherein each of the first universal primer and the second universal primers comprises one or more functional sequences and/or groups at its 5' end or in its 5' end portion wherein the one or more functional sequences are selected from sequences comprising downstream oligonucleotide binding sites, sequences comprising restriction enzyme recognition sites, and reaction identification sequences.

15. The method according to claim 12, wherein the ratio of 10:1 to 500:1 is 12:1 to 275:1.

16. A method for generating amplicon constructs from an RNA target sequence, the method comprising
preparing the first target-specific primer and the second target-specific primer using the method of claim 12;
providing an RNA target sequence; and
generating the amplicon constructs by performing a reverse transcription PCR in the presence of the RNA target sequence, the first target-specific primer, and the second target-specific primer.

\* \* \* \* \*